United States Patent
Müller et al.

[11] Patent Number: 6,028,093
[45] Date of Patent: Feb. 22, 2000

[54] FUNGICIDE COMPOSITIONS

[75] Inventors: Bernd Müller, Frankenthal; Hubert Sauter, Mannheim; Eberhard Ammermann, Heppenheim; Gisela Lorenz, Hambach; Siegfried Strathmann, Limburgerhof; Klaus Schelberger, Gönnheim; Maria Scherer, Landau; Dietrich Mappes, Westheim; Joachim Leyendecker, Ladenburg; Herbert Bayer, Mannheim; Ruth Müller, Friedelsheim, all of Germany

[73] Assignee: BASF Aktiengesellschaft, Ludwigshaften, Germany

[21] Appl. No.: 09/171,563

[22] PCT Filed: Apr. 23, 1997

[86] PCT No.: PCT/EP97/02048

§ 371 Date: Oct. 21, 1998

§ 102(e) Date: Oct. 21, 1998

[87] PCT Pub. No.: WO97/40678

PCT Pub. Date: Nov. 6, 1997

[30] Foreign Application Priority Data

Apr. 26, 1996 [DE] Germany ............ 196 16 689
Apr. 29, 1996 [DE] Germany ............ 196 17 069
Sep. 2, 1996 [DE] Germany ............ 196 35 505

[51] Int. Cl.$^7$ .......... A01N 37/18; A01N 37/38; A01N 43/653

[52] U.S. Cl. .......... 514/384; 514/407; 514/479; 514/716; 514/718; 548/263.2; 548/264.2; 548/366.1; 548/371.1; 560/27; 560/29; 560/35; 560/43; 560/159; 564/254; 564/256

[58] Field of Search ............ 514/384, 407, 514/479, 717, 718; 548/263.2, 264.2, 336.1, 371.1; 560/159; 564/256

[56] References Cited

U.S. PATENT DOCUMENTS

| 3,513,241 | 5/1970 | Hoyer et al. | 424/300 |
| 5,491,165 | 2/1996 | Dehne et al. | 514/479 |
| 5,650,423 | 7/1997 | Dehne et al. | 514/376 |

FOREIGN PATENT DOCUMENTS

| 289 879 | 11/1988 | European Pat. Off. . |
| 610 764 | 8/1994 | European Pat. Off. . |
| 1 567 169 | 12/1970 | Germany . |
| 195 28 651 | 2/1997 | Germany . |
| 95/21153 | 8/1995 | WIPO . |
| 95/21154 | 8/1995 | WIPO . |
| 96/01256 | 1/1996 | WIPO . |
| 96/01258 | 1/1996 | WIPO . |
| 97/11606 | 4/1997 | WIPO . |

OTHER PUBLICATIONS

Research Disclosure 1993 Apr., No. 348, 2244.

Primary Examiner—Johann Richter
Assistant Examiner—Jane C. Oswecki
Attorney, Agent, or Firm—Keil & Weinkauf

[57] ABSTRACT

Fungicidal mixtures, comprising
a) a carbamate of the formula I

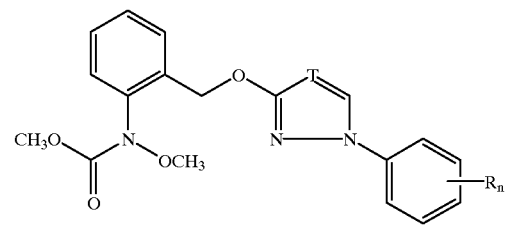

(I)

where T is CH or N, n is 0, 1 or 2 and R is halogen, $C_1$–$C_4$-alkyl or $C_1$–$C_4$-haloalkyl, it being possible for the radicals R to be different when n is 2, and/or b) an oxime ether of the formula II,

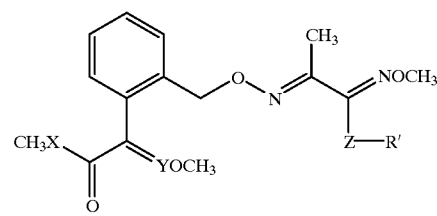

(II)

where the substituents have the following meanings:
X is oxygen or amino;
Y is CH or N;
Z is oxygen, sulfur, amino or $C_1$–$C_4$-alkylamino
R' is $C_1$–$C_6$-alkyl, $C_1$–$C_6$-haloalkyl, $C_3$–$C_6$-alkenyl, $C_2$–$C_6$-haloalkenyl, $C_3$–$C_6$-alkynyl, $C_3$–$C_6$-haloalkynyl, $C_3$–$C_6$-cycloalkyl-methyl, or is benzyl which can be partially or fully halogenated and/or can have attached to it one to three of the following radicals: cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio; and c) a carbamate of the formula III $(CH_3)_2N$—$CH_2CH_2CH_2$—$NH$—$CO_2$—$CH_2CH_2CH_3$ (III)

in a synergistically active amount.

20 Claims, No Drawings

FUNGICIDE COMPOSITIONS

This application is a 371 of PCT/EP 97/02048 filed Apr. 23, 1997.

The present invention relates to a fungicidal mixture which comprises a) a carbamate of the formula I

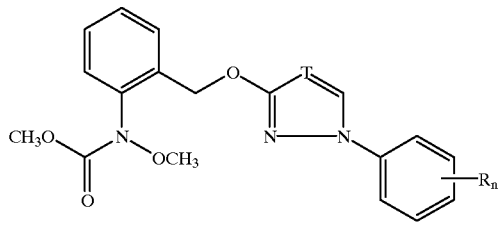

where T is CH or N, n is 0, 1 or 2 and R is halogen, $C_1$–$C_4$-alkyl or $C_1$–$C_4$-haloalkyl, it being possible for the radicals R to be different when n is 2, and/or b) an oxime ether of the formula II,

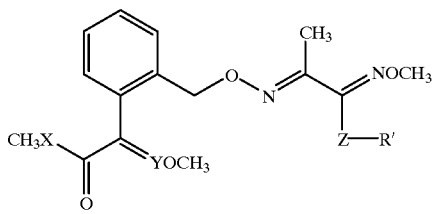

where the substituents have the following meanings:

X is oxygen or amino (NH);
Y is CH or N;
Z is oxygen, sulfur, amino (NH) or $C_1$–$C_4$-alkylamino (N—$C_1$–$C_4$-alkyl);
R' is $C_1$–$C_6$-alkyl, $C_1$–$C_6$-haloalkyl, $C_3$–$C_6$-alkenyl, $C_2$–$C_6$-haloalkenyl, $C_3$–$C_6$-alkynyl, $C_3$–$C_6$-haloalkynyl, $C_3$–$C_6$-cycloalkylmethyl, or is benzyl which can be partially or fully halogenated and/or can have attached to it one to three of the following radicals: cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

c) a carbamate of the formula III $$(CH_3)_2N-CH_2CH_2CH_2-NH-CO_2-CH_2CH_2CH_3 \quad III$$

in a synergistically active amount.

Moreover, the invention relates to methods of controlling harmful fungi with mixtures of the compounds I and/or II and III and to the use of the compounds I and/or II and the compound III for the preparation of such mixtures.

The compounds of the formula I, their preparation and their action against harmful fungi have been disclosed in the literature (WO-A 96/01,256 and WO-A 96/01,258).

Compounds of the formula II, their preparation and their action against harmful fungi have been described in WO-A 95/21,153, WO-A 95/21,154 and DE 1 95 28 651.0.

The compound III (German Laid-Open Application DOS 15 67 169, common name: propamocarb), its preparation and its action against harmful fungi have also been disclosed.

It was an object of the present invention to provide mixtures which have an improved activity gainst harmful fungi combined with a reduced total amount of active ingredients applied (synergistic mixtures) with a view to reducing the rates of application and to improving the spectrum of action of the known compounds.

Accordingly, we have found that this object is achieved by the mixture defined at the outset. Moreover, we have found that better control of the harmful fungi is possible by applying the compounds I and/or II and the compound III simultaneously together or separately or by applying the compounds I and/or II and the compound III in succession than when the individual compounds are used.

In particular, the formula I represents carbamates in which the combination of the substituents corresponds to one line of the table which follows:

| No. | T | $R_n$ |
|---|---|---|
| I.1 | N | 2-F |
| I.2 | N | 3-F |
| I.3 | N | 4-F |
| I.4 | N | 2-Cl |
| I.5 | N | 3-Cl |
| I.6 | N | 4-Cl |
| I.7 | N | 2-Br |
| I.8 | N | 3-Br |
| I.9 | N | 4-Br |
| I.10 | N | 2-$CH_3$ |
| I.11 | N | 3-$CH_3$ |
| I.12 | N | 4-$CH_3$ |
| I.13 | N | 2-$CH_2CH_3$ |
| I.14 | N | 3-$CH_2CH_3$ |
| I.15 | N | 4-$CH_2CH_3$ |
| I.16 | N | 2-$CH(CH_3)_2$ |
| I.17 | N | 3-$CH(CH_3)_2$ |
| I.18 | N | 4-$CH(CH_3)_2$ |
| I.19 | N | 2-$CF_3$ |
| I.20 | N | 3-$CF_3$ |
| I.21 | N | 4-$CF_3$ |
| I.22 | N | 2,4-$F_2$ |
| I.23 | N | 2,4-$Cl_2$ |
| I.24 | N | 3,4-$Cl_2$ |
| I.25 | N | 2-Cl, 4-$CH_3$ |
| I.26 | N | 3-Cl, 4-$CH_3$ |
| I.27 | CH | 2-F |
| I.28 | CH | 3-F |
| I.29 | CH | 4-F |
| I.30 | CH | 2-Cl |
| I.31 | CH | 3-Cl |
| I.32 | CH | 4-Cl |
| I.33 | CH | 2-Br |
| I.34 | CH | 3-Br |
| I.35 | CH | 4-Br |
| I.36 | CH | 2-$CH_3$ |
| I.37 | CH | 3-$CH_3$ |
| I.38 | CH | 4-$CH_3$ |
| I.39 | CH | 2-$CH_2CH_3$ |
| I.40 | CH | 3-$CH_2CH_3$ |
| I.41 | CH | 4-$CH_2CH_3$ |
| I.42 | CH | 2-$CH(CH_3)_2$ |
| I.43 | CH | 3-$CH(CH_3)_2$ |
| I.44 | CH | 4-$CH(CH_3)_2$ |
| I.45 | CH | 2-$CF_3$ |
| I.46 | CH | 3-$CF_3$ |
| I.47 | CH | 4-$CF_3$ |
| I.48 | CH | 2,4-$F_2$ |
| I.49 | CH | 2,4-$Cl_2$ |
| I.50 | CH | 3,4-$Cl_2$ |
| I.51 | CH | 2-Cl, 4-$CH_3$ |
| I.52 | CH | 3-Cl, 4-$CH_3$ |

The compounds I.12, I.23, I.32 and I.38 are especially preferred.

In particular, the general formula II represents methoxyacrylates and oxime ethers where X is oxygen and Y is CH, or X is amino and Y is N.

Moreover, preferred compounds II are those where Z is oxygen.

Equally, preferred compounds II are those where R' is alkyl or benzyl.

Particularly preferred with a view to their use in the synergistic mixtures according to the invention are the compounds II which are compiled in the tables below:

Table 2.

Compounds of the formula IIA where ZR' for each compound corresponds to one line of Table A.

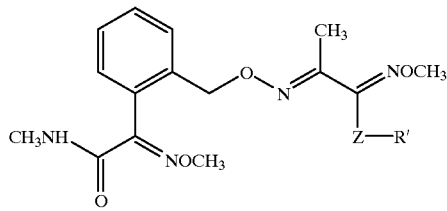

(IIA)

Table 3.

Compounds of the formula IIB where ZR' for each compound corresponds to one line of Table A

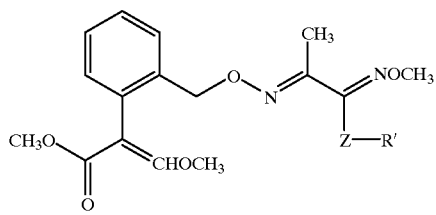

(IIB)

TABLE A

| No. | ZR' |
|---|---|
| II.1 | O—CH$_2$CH$_2$CH$_3$ |
| II.2 | O—CH(CH$_3$)$_2$ |
| II.3 | O—CH$_2$CH$_2$CH$_2$CH$_3$ |
| II.4 | O—CH(CH$_3$)CH$_2$CH$_3$ |
| II.5 | O—CH$_2$CH(CH$_3$)$_2$ |
| II.6 | O—C(CH$_3$)$_3$ |
| II.7 | S—C(CH$_3$)$_3$ |
| II.8 | O—CH(CH$_3$)CH$_2$CH$_2$CH$_3$ |
| II.9 | O—CH$_2$C(CH$_3$)$_3$ |
| II.10 | O—CH$_2$C(Cl)=CCl$_2$ |
| II.11 | O—CH$_2$CH=CH—Cl (trans) |
| II.12 | O—CH$_2$C(CH$_3$)=CH$_2$ |
| II.13 | O—CH$_2$-(cyclopropyl) |
| II.14 | O—CH$_2$—C$_6$H$_5$ |
| II.15 | O—CH$_2$-[4-F—C$_6$H$_4$] |
| II.16 | O—CH$_2$CH$_3$ |
| II.17 | O—CH(CH$_2$CH$_3$)$_2$ |

Relative to the C=Y double bond, the compounds of the formula II can exist in the E or the Z configuration (relative to the carboxylic acid function). Accordingly, they can be used in the mixture according to the invention in each case either in the form of pure E or Z isomers or as an E/Z isomer mixture. Preferred in each case is the E/Z isomer mixture or the E isomer, the E isomer being especially preferred in the case of the compound II.

The C=N double bonds of the oxime ether groups in the side chain of the compounds II can exist in each case in the form of pure E or Z isomers or as E/Z isomer mixtures. The compounds II can be used as isomer mixtures and also as pure isomers in the mixtures according to the invention. With a view to their use, compounds II which are particularly preferred are those where the terminal oxime ether group in the side chain is in the cis configuration (OCH$_3$ group relative to ZR').

Due to the basic character, the compounds I and II are capable of forming adducts or salts with inorganic or organic acids or with metal ions.

Examples of inorganic acids are hydrohalic acids such as hydrofluoric acid, hydrochloric acid, hydrobromic acid and hydroiodic acid, sulfuric acid, phosphoric acid and nitric acid.

Suitable organic acids are, for example, formic acid, car-boxylic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals having from 1 to 20 carbon atoms), arylsulfonic acids or -disulfonic acids (aromatic radicals such as phenyl and naphthyl which have attached to them one or two sulfo groups), alkylphosphonic acids (phosphonic acids having straight-chain or branched alkyl radicals of from 1 to 20 carbon atoms), arylphosphonic acids or -diphosphonic acids (aromatic radicals such as phenyl and naphthyl which have attached to them one or two phosphonic acid radicals), it being possible for the alkyl or aryl radicals to have attached to them further substituents, eg. p-toluenesulfonic acid, salicylic acid, p-aminosalicylic acid, 2-phenoxybenzoic acid, 2-acetoxybenzoic acid etc.

Suitable metal ions are, in particular, the ions of the elements of the second main group, in particular calcium and magnesium, and of the third and fourth main group, in particular aluminum, tin and lead, and of the first to eighth sub-group, in particular chromium, manganese, iron, cobalt, nickel, copper, zinc and others. Especially preferred are the metal ions of the elements of the sub-groups of the fourth period. The metals can in this case be in the various valences which they can assume.

When preparing the mixtures, it is preferred to employ the pure active ingredients I, II and III, with which further active ingredients against harmful fungi or other pests such as insects, arachnids or nematodes, or else herbicidal or growth-regulating active ingredients or fertilizers can be admixed, if so desired.

The mixtures of the compounds I and/or II and III, or the simultaneous joint or separate use of the compounds I and/or II and III, are distinguished by an outstanding activity against a broad spectrum of phytopathogenic fungi, in particular from the classes of the Ascomycetes, Deuteromycetes, Phycomycetes and Basidiomycetes. Some of them act systemically and can therefore be employed as foliar- and soil-acting fungicides.

They are especially important for controlling a large number of fungi in a variety of crop plants such as cotton, vegetable species (eg. cucumbers, beans and curcubits), barley, grass, oats, coffee, corn, fruit species, rice, rye, soybeans, grapevine, wheat, ornamentals, sugar cane, and a variety of seeds.

They are particularly suitable for controlling the following phytopathogenic fungi: Erysiphe graminis (powdery mildew) on cereals, Erysiphe cichoracearum and Sphaerotheca fuliginea on curcubits, Podosphaera leucotricha on apples, Puccinia species on cereals, Rhizoctonia species on cotton, rice and lawn, Ustilago species on cereals and sugar cane, Venturia inaequalis (scab) on apples, Helminthosporium species on cereals, Septoria nodorum on wheat, Botrytis cinerea (gray mold) on strawberries, vegetables, ornamentals and grapevines, Cercospora arachidicola on peanuts, Pseudocercosporella herpotrichoides on wheat and barley, Pyricularia oryzae on rice, Phytophthora infestans on potatoes and tomatoes, Pseudoperonospora species on cucurbits and hops, Plasmopara viticola on grapevines, Alternaria species on vegetables and fruit, and Fusarium and Verticillium species.

Furthermore, they can be used in the protection of materials (eg. in the protection of wood), for example against Paecilomyces variotii.

The compounds I and/or II and III can be applied simultaneously together or separately or in succession, the sequence, in the case of separate application, generally not having any effect on the result of the control measures.

The compounds I and/or II and III are normally used in a weight ratio of from 200:1 to 0.1:1, preferably 100:1 to 1:1, in particular 50:1 to 5:1 (III:I and/or II).

The application rates of the mixtures according to the invention are, in the case of the compounds I and/or II, in general from 0.005 to 0.5 kg/ha, preferably 0.01 to 0.5 kg/ha, in particular 0.01 to 0.3 kg/ha, depending on the nature of the desired effect.

Correspondingly, in the case of the compound III, the application rates are from 0.1 to 10 kg/ha, preferably 0.5 to 5 kg/ha, in particular 1 to 4 kg/ha.

For seed treatment, the application rates of the mixture are generally from 0.001 to 100 g/kg seed, preferably 0.01 to 50 g/kg, in particular 0.01 to 10 g/kg.

If phytopathogenic harmful fungi are to be controlled, the separate or joint application of the compounds I and/or II and III or of the mixtures of the compounds I and/or II and III is effected by spraying or dusting the seeds, the plants or the soils before or after sowing of the plants, or before or after plant emergence.

The fungicidal synergistic mixtures according to the invention, or the compounds I and/or II and III, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and applied by spraying, atomizing, dusting, spreading or pouring. The use form depends on the intended purpose; in any case, it should guarantee as fine and uniform as possible a distribution of the mixture according to the invention.

The formulations are prepared in a manner known per se, eg. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, of alkyl- and alkylarylsulfonates, of alkyl, lauryl ether and fatty alcohol sulfates, and salts of sulfated hexa-, hepta- and octadecanols or fatty alcohol glycol ethers, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl polyglycol ethers or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or jointly grinding the compounds I and/or II or III or the mixture of the compounds I and/or II and III with a solid carrier.

Granules (eg. coated granules, impregnated granules or homogeneous granules) are normally prepared by binding the active ingredient, or active ingredients, to a solid carrier.

Fillers or solid carriers are, for example, mineral earths such as silica gel, silicas, silicates, talc, kaolin, limestone, lime, chalk, bole, loess, clay, dolomite, diatomaceous earth, calcium sulfate, magnesium sulfate, magnesium oxide, ground synthetic materials, and fertilizers such as ammonium sulfate, ammonium phosphate, ammonium nitrate, ureas, and products of vegetable origin such as cereal meal, tree bark meal, wood meal and nutshell meal, cellulose powders or other solid carriers.

The formulations generally comprise from 0.1 to 95% by weight, preferably 0.5 to 90% by weight, of one of the compounds I and/or II or III, or of the mixture of the compounds I and/or II and III. The active ingredients are employed in a purity of from 90% to 100%, preferably 95% to 100% (according to NMR or HPLC spectrum).

The compounds I and/or II and III, or the mixtures, or the corresponding formulations, are applied by treating the harmful fungi or the plants, seeds, soils, areas, materials or spaces to be kept free from them with a fungicidally active amount of the mixture, or of the compounds I and/or II and III in the case of separate application. Application can be effected before or after infection by the harmful fungi.

The fungicidal activity of the compounds and of the mixtures is demonstrated by the following experiments:

The active ingredients, separately or together, are formulated as a 10% emulsion in a mixture of 70% by weight of cyclohexanone, 20% by weight of "NEKANIL® LN" ("Lutensol® AP6", wetting agent having emulsifying and dispersing action based on ethoxylated alkylphenols) and 10% by weight of "EMULPMOR® EL" "(EMULAN® EL" emulsifier based on ethoxylated fatty alcohols) and diluted with water to give the desired concentration.

Evaluation is carried out by determining the infected leaf areas in percent. These percentages are converted into efficacies. The expected efficacies of the mixtures of the active ingredients are determined using Colby's formula [R. S. Colby, Weeds 15, 20–22 (1967)] and compared with the observed efficacies.

Colby's formula:

$$E = x + y - x \cdot y / 100$$

E expected efficacy, expressed in % of the untreated control, when using the mixture of the active ingredients A and B at concentrations of a and b x efficacy, expressed in % of the untreated control, when using active ingredient A at a concentration of a y efficacy, expressed in % of the untreated control, when using active ingredient B at a concentration of b The efficacy (W) is calculated as follows using Abbot's formula:

$$W = (1 - \alpha) \cdot 100 / \beta$$

$\alpha$ is the fungal infection of the treated plants in % and
$\beta$ is the fungal infection of the untreated (control) plants in %

An efficacy of 0 means that the infection level of the treated plants corresponds to that of the untreated control plants; an efficacy of 100 means that the treated plants are not infected.

EXAMPLES 1–10

Efficacy Against Phytophthora Infestans on Tomatoes

Leaves of potted tomato plants cv. "Große Fleischtomate" were sprayed to run-off with an aqueous suspension made with a stock solution of 10% active ingredient, 63% cyclohexanone and 27% emulsifier. The next day, the leaves were inoculated with an aqueous zoospore suspension of Phytophthora infestans. The plants were subsequently placed into a water-vapor-saturated chamber at from 16 to 18° C. After 6 days, the blight had developed to such an extent on the untreated, but inoculated, control plants that it was possible to determine the disease level visually in %.

The visually determined values for the percentage of diseased leaf area were transformed into efficacies as % of the untreated control. An efficacy of 0 is the same disease level as in the untreated control, an efficacy of 100 is a disease level of 0%. The expected efficacies for combinations of active ingredients were determined using Colby's formula (Colby, S. R. (Calculating synergistic and antagonistic responses of herbicide Combinaations", Weeds, 15, p. 20–22, 1967) and compared with the observed efficacies.

In the following, A represents example II.2 of Table 2, ie. the compound of formula IIA wherein ZR' denotes OCH$(CH_3)_2$, and B represents example II.4 of Table 2, ie. the compound of formula IIA wherein ZR' denotes OCH($CH_3$)$CH_2CH_3$.

TABLE 4

| Ex. | Active ingredient | Concentration of active ingredient in the spray mixture in ppm | Efficacy in % of the untreated control |
|---|---|---|---|
| 1v | Control (untreated) | (disease level 98%) | 0 |
| 2v | A | 16 | 8 |
|    |   | 4 | 8 |
|    |   | 1 | 0 |
| 3v | B | 16 | 39 |
|    |   | 4 | 0 |
|    |   | 1 | 0 |
| 4v | III = propamocarb | 125 | 18 |
|    |   | 63 | 8 |
|    |   | 31 | 8 |
|    |   | 16 | 0 |

TABLE 5

| Ex. | Concentration of active ingredient in the spray mixture in ppm | Observed efficacy | Calculated efficacy*) |
|---|---|---|---|
| 5 | 16A + 16III | 49 | 8 |
| 6 | 16A + 31III | 49 | 15 |
| 7 | 16A + 63III | 39 | 15 |
| 8 | 16A + 125III | 69 | 24 |
| 9 | 16B + 31III | 59 | 43 |
| 10 | 16B + 63III | 59 | 43 |

*) calculated using Colby's formula

The results of Examples 1–10 demonstrate that the observed efficacy in all mixing ratios exceeds the efficacy precalculated using Colby's formula.

We claim:

1. A fungicidal composition comprising
a) a carbamate of the formula I

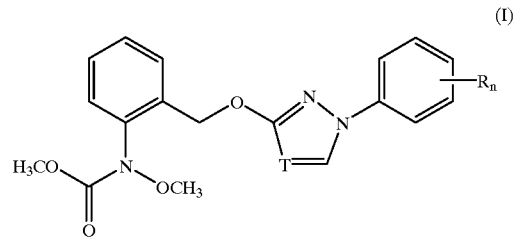

where T is CH or N, n is 0, 1 or 2 and R is halogen, $C_1$–$C_4$-alkyl or $C_1$–$C_4$-haloalkyl, it being possible for the radicals R to be different when n is 2, or
b) an oxime ether of the formula II

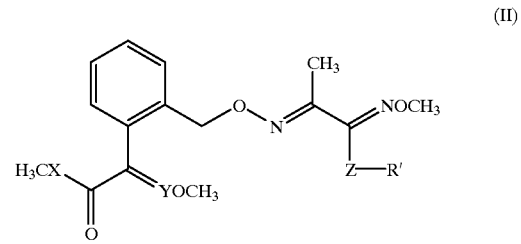

where the substituents have the following meaning:
X is oxygen or amino
Y is CH or N;
Z is oxygen, sulfur, amino or $C_1$–$C_4$-alkylamino;
R' is $C_1$–$C_6$-alkyl, $C_1$–$C_6$-haloalkyl, $C_3$–$C_6$-alkenyl, $C_2$–$C_6$-haloalkenyl, $C_3$–$C_6$-alkynyl, $C_3$–$C_6$-haloalkynyl, $C_3$–$C_6$-cycloalkylmethyl, or benzyl which may be partially or fully halogenated and/or may carry one to three of the following radicals: cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

and
c) a carbamate of the formula III $$(H_3C)_2N—CH_2CH_2CH_2—NHCO_2—CH_2CH_2CH_3 \quad \text{(III)}$$

or comprising the carbamate I, the oxime ether II and the carbamate III, in a synergistically active amount.

2. The fungicidal composition defined in claim 1 wherein the weight ratio of the compound III to the compound I or II or, if present, the compound I and the compound II, is 200:1 to 0.1:1.

3. A method of controlling harmful fungi, which comprises treating the harmful fungi, their environment, or the plants, seeds, soils, areas, materials or spaces to be kept free from fungal infection with a compound I or a compound II or, if present, the compound I and the compound II, and the compound III as set forth in claim 1 in a synergistically active amount.

4. The method defined in claim 3, wherein the compound I or the compound II or, if present, the compound I and the compound II, and the compound III are applied simultaneously together or separately, or in succession.

5. The method defined in claim 3, wherein of from 0.005 to 0.5 kg/ha of the compound I or the compound II or, if present, the compound I and the compound II, are applied.

6. The method defined in claim 3, wherein of from 0.1 to 10 kg/ha of the compound III are applied.

7. The composition defined in claim 1, comprising the carbamate I and the carbamate III.

8. The composition defined in claim 1, comprising the oxime ether II and the carbamate III.

9. The composition defined in claim 1, comprising the carbamate I, the oxime ether II and the carbamate III.

10. The composition defined in claim 1, wherein X is oxygen and Y is CH.

11. The composition defined in claim 1, wherein X is oxygen, Y is CH, Z is oxygen and R' is alkyl or benzyl.

12. The composition defined in claim 7, wherein X is oxygen, Y is CH, Z is oxygen and R' is alkyl or benzyl.

13. The composition defined in claim 9, wherein X is oxygen, Y is CH, z is oxygen and R' is alkyl or benzyl.

14. The composition defined in claim 1, wherein X is amino and Y is N.

15. The composition defined in claim 1, wherein X is amino, Y is N, Z is oxygen and R' is alkyl or benzyl.

16. The composition defined in claim 7, wherein X is amino, Y is N, Z is oxygen and R' is alkyl or benzyl.

17. The composition defined in claim 9, wherein X is amino, Y is N, Z is oxygen and R' is alkyl or benzyl.

18. The composition defined in claim 1, wherein R is selected from the group consisting of fluoro, chloro, bromo, methyl, ethyl, isopropyl and trifluoromethyl.

19. The composition defined in claim 8, wherein R is selected from the group consisting of fluoro, chloro, bromo, methyl, ethyl, isopropyl and trifluoromethyl.

20. The composition defined in claim 9, wherein R is selected from the group consisting of fluoro, chloro, bromo, methyl, ethyl, isopropyl and trifluoromethyl.

* * * * *

UNITED STATES PATENT AND TRADEMARK OFFICE
CERTIFICATE OF CORRECTION

PATENT NO. : 6,028,093
DATED : February 22, 2000
INVENTOR(S) : MÜLLER et al.

It is certified that error appears in the above-identified patent and that said Letters Patent is hereby corrected as shown below:

Column 8, claim 1, line 34, after "amino", insert a semicolon --;--.
Column 8, claim 1, line 42, change both occurrences of "$C_l$-$C_4$" to --$C_1$-$C_4$--.

Signed and Sealed this

Thirtieth Day of January, 2001

Attest:

Q. TODD DICKINSON

*Attesting Officer*    *Director of Patents and Trademarks*